(12) United States Patent
List (10) Patent No.: US 11,324,883 B2
(45) Date of Patent: May 10, 2022

(54) AMBULATORY INFUSION SYSTEM INITIALIZATION

(71) Applicant: Roche Diabetes Care, Inc., Indianapolis, IN (US)

(72) Inventor: Hans List, Oberzent (DE)

(73) Assignee: ROCHE DIABETES CARE, INC., Indianapolis, IN (US)

(*) Notice: Subject to any disclaimer, the term of this patent is extended or adjusted under 35 U.S.C. 154(b) by 279 days.

(21) Appl. No.: 16/463,690

(22) PCT Filed: Dec. 13, 2017

(86) PCT No.: PCT/EP2017/082600
§ 371 (c)(1),
(2) Date: May 23, 2019

(87) PCT Pub. No.: WO2018/108996
PCT Pub. Date: Jun. 21, 2018

(65) Prior Publication Data
US 2019/0321544 A1    Oct. 24, 2019

(30) Foreign Application Priority Data
Dec. 14, 2016 (EP) ..................................... 16203958

(51) Int. Cl.
*A61M 5/145* (2006.01)
*A61M 5/142* (2006.01)
*A61M 5/168* (2006.01)

(52) U.S. Cl.
CPC ........ *A61M 5/1456* (2013.01); *A61M 5/1454* (2013.01); *A61M 5/14216* (2013.01); *A61M 5/14248* (2013.01); *A61M 5/16809* (2013.01)

(58) Field of Classification Search
CPC ............ A61M 5/1456; A61M 5/14216; A61M 5/14248; A61M 5/1454; A61M 5/16809
See application file for complete search history.

(56) References Cited

U.S. PATENT DOCUMENTS 4,137,913 A * 2/1979 Georgi .............. A61M 5/14216
                                                    128/DIG. 12
4,396,385 A *  8/1983 Kelly .................... A61M 5/172
                                                    604/152

(Continued)

FOREIGN PATENT DOCUMENTS

EP         0 925 798       5/2003
JP        2012-500099      1/2012

(Continued)

OTHER PUBLICATIONS

Office Action in related JP2019-531613 dated Mar. 2, 2021.

*Primary Examiner* — James D Ponton
(74) *Attorney, Agent, or Firm* — Woodard, Emhardt, Henry, Reeves & Wagner, LLP (57) ABSTRACT

Disclosed is a method for initializing an ambulatory infusion system. The method includes providing a liquid drug cartridge including a cartridge body, and a cartridge piston. The method further includes providing a dosing unit including a metering pump unit with a dosing cylinder and a dosing piston. The dosing unit further includes a valve unit configured for switching between a filling state and a draining state. The filling port being fluidically coupled with the dosing cylinder in the filling state and the draining port is fluidically coupled with the dosing cylinder in the draining state. The method further includes
a) exerting an initialization force displacing the cartridge piston, and
b) increasing a fluidic volume of the dosing cylinder by displacing the dosing piston, thereby sucking liquid out of the liquid drug cartridge into the dosing cylinder and further displacing the cartridge piston, without the initialization pushing force being exerted.

17 Claims, 3 Drawing Sheets

(56) References Cited

U.S. PATENT DOCUMENTS

| | | | | |
|---|---|---|---|---|
| 4,437,859 A | * | 3/1984 | Whitehouse | A61M 5/14526 |
| | | | | 604/131 |
| 8,622,966 B2 | | 1/2014 | Causey et al. | |
| 2008/0071228 A1 | | 3/2008 | Shang-Ren et al. | |
| 2014/0364808 A1 | * | 12/2014 | Niklaus | A61M 5/1454 |
| | | | | 604/135 |
| 2014/0378943 A1 | | 12/2014 | Geipel | |

FOREIGN PATENT DOCUMENTS

| | | |
|---|---|---|
| RU | 2015103542 | 6/2015 |
| WO | WO 2010/008575 A1 | 1/2010 |
| WO | WO 2010/077279 A1 | 7/2010 |

* cited by examiner

AMBULATORY INFUSION SYSTEM INITIALIZATION

FIELD OF DISCLOSURE

The present disclosure lies in the field of ambulatory infusion devices and ambulatory infusion systems for infusing a liquid drug into a patient's body over an extended time period. A typical field of application is the therapy of Diabetes Mellitus via Continuous Subcutaneous Insulin Infusion (CSII).

BACKGROUND, PRIOR ART

Ambulatory infusion devices are well known in the art for example in the therapy of Diabetes Mellitus by Continuous Subcutaneous Insulin Infusion (CSII) as well as in pain therapy or cancer therapy and are available from a number of supplies, such as Roche Diabetes Care GmbH, Germany, or Medtronic MiniMed Inc., CA, USA.

According to a classic and well-established design, those ambulatory infusion devices or systems are typically of the syringe-driver type. A number of drawbacks of such devices are known in the art. In particular, they have a limited precision because they involve delivering very small drug amounts, typically in the nanoliter range, out of a drug cartridge having an overall drug volume in the millilitre range. Therefore, additional concepts and architectures have been proposed which use a dedicated dosing unit downstream from the drug reservoir. The dosing unit may comprise, e.g., a micro membrane pump or a micro piston pump and is adapted to couple to a drug reservoir and is further especially designed for precise metering of small volumes. While several designs for such dosing units are known in the art, they are rather complex, most of them are expensive and/or critical with respect to large scale.

The EP1970677 discloses a system with a miniaturized metering piston pump with a dosing cylinder that is repeatedly coupled to and filled from a larger reservoir (primary reservoir), followed by coupling the dosing cylinder to an infusion site and infusing the liquid drug out of the dosing cylinder in incremental steps and over an extended time period. For alternatively coupling the dosing cylinder to the reservoir and the infusion site, a valve system is proposed. Filling of the dosing cylinder is achieved.

An ambulatory infusion system in accordance with the principles disclosed in EP1970677 has the advantage that the metering is carried out from a comparatively small reservoir (the dosing cylinder) of substantially smaller cross sectional area as compared to e. g. a standard syringe driver as explained before. In dependence of a diabetic's individual therapeutic needs, the filling volume of the dosing cylinder is sufficient for a number of hours up to a day or more, before it is refilled from the primary reservoir.

SUMMARY OF DISCLOSURE

Since the dosing is not carried out directly out of the primary reservoir but out of the dosing cylinder as volumetric metering pump, a variety of different primary reservoirs may in principle be used in combination with a dosing unit as explained before, including, e. g. flexible or semi-rigid bags or pouches, e. g. according to the disclosure of EP 2455126 A1.

However, for a variety of practical reasons, in particular commercial availability and ease of handling for the user, so-called pen-type cartridges with a cylindrical cartridge body, a drug cartridge outlet that is sealed by a pierceable septum, and a cartridge piston that is arranged in an inner volume of the cartridge body in a sealing and displaceable manner, are attractive. Such pen-cartridge are readily available with a variety of liquid drugs, in particular liquid insulin formulations, and have a typical filling volume in a range of e. g. 1 to 3 ml. Those pen-type cartridges are typically designed for use in a hand-held pen-type injection device as frequently used, e. g. in diabetes therapy by multiple daily insulin injections.

When used in combination with a downstream dosing system as explained before, each filling or re-filling of the dosing cylinder involves sucking liquid drug out of the cartridge into the dosing cylinder by way of a pressure difference resulting from increasing the fluidic volume of the dosing cylinder. As liquid drug is displaced out of the cartridge, the cartridge piston needs to compensate for the reduced liquid volume by a corresponding displacement. In principle, the cartridge piston may be displaced by the pulling force that is exerted by the (incompressible) liquid drug when being sucked into the dosing cylinder.

In practice, however, it is found that the pulling force for overcoming the sticking frictional force may be higher than the force that may result from the under pressure in the dosing cylinder. Further, even if a corresponding force can in principle be generated, it is desirable to work with pressure gradients that are as small as possible in order to avoid or at least limit the outgassing of gas, in particular air that is solved in the liquid drug.

It has therefore been proposed to continuously exert a pushing force onto the cartridge pressure, thereby biasing the cartridge piston in a cartridge piston advancement direction (i. e. the direction in which the cartridge piston is displaced for expelling liquid), thereby decreasing the pulling force that needs to be generated by the dosing unit. This pushing force should be substantially constant over the whole displacement range of the cartridge piston. Furthermore, a compact design is highly desirable. Corresponding biasing devices are accordingly comparatively complex and still require a considerable installation space. Exemplary designs are disclosed, e. g. in the WO2013/127428A1.

It is an overall objective of the present invention to improve the situation regarding the use of liquid drug cartridges in combination with a dosing unit and in particular regarding the displacement of the cartridge piston. Favourably, disadvantages of the prior art are avoided fully or partly.

This objective is achieved in a general way by the subject of the independent claims. Particular exemplary embodiments are defined by the corresponding dependent claims as well as the embodiments described in this description and the figures.

In a general way, the objective is achieved based on the insight that the problem of overcoming the sticking friction is particularly given when moving the cartridge piston for the first time after a potentially long period of storage, often under comparatively adverse environmental conditions. This situation occurs each time the liquid drug cartridge is exchanged. Once the initial sticking friction has been overcome, the sticking friction that needs to be overcome each time the dosing cylinder is refilled is considerably smaller and can be generated as under pressure by the dosing unit without requiring additional measures.

According to an aspect, the overall objective is achieved by providing a method for initializing an ambulatory infusion system. The method includes the steps of providing a liquid drug cartridge, the liquid drug cartridge including a cartridge body and a cartridge piston. The cartridge piston is arranged inside the cartridge body in a sealing and displaceable manner. The liquid drug cartridge may e. g. be a pen-type cartridge as known in the art and widely available.

The method further includes providing a dosing unit, the dosing unit including a metering pump unit with a dosing cylinder and a dosing piston. The dosing piston is arranged inside the dosing cylinder in a sealing and displaceable manner. The dosing unit further includes a valve unit with a filling port, and a draining port. The valve unit is configured for switching between a filling state and an alternative draining state, wherein the filling port is fluidic coupled with an inner volume of the dosing cylinder in the filling state and the draining port is fluidic coupled with the inner volume of the dosing cylinder in the draining state.

The method further includes providing an initialization force member and includes executing the steps of:

a) exerting, with the initialization force member, an initialization pushing force onto the cartridge piston thereby displacing the cartridge piston inside the cartridge body in a cartridge piston advancement direction by an initialization distance;

b) increasing a fluidic volume of the dosing cylinder by displacing the dosing piston, thereby sucking liquid drug out of the liquid drug cartridge into the dosing cylinder and further displacing the cartridge piston inside the cartridge body in the cartridge piston advancement direction, without the initialization pushing force being exerted.

The dosing cylinder forms a blind hole in which the dosing piston is received. The fluidic volume of the dosing cylinder is the volume between the dosing piston and the (proximal) ground of the dosing cylinder bore. The fluidic volume of the dosing cylinder accordingly varies with the displacement position of the dosing cylinder. It is minimal (typically zero or close to zero) in a most advanced position of the dosing piston and maximal in a most retracted position of the dosing piston.

In step (a), the initial sticking friction is overcome by the initialization pushing force that is exerted by the initialization force member. As explained further below in more detail, step (a) generally includes a displacement of the cartridge body against the cartridge piston advancement direction. This step is generally carried out manually as part of exchanging the liquid drug cartridge respectively preparing the ambulatory infusion system for use. In particular, the initialization pushing force is a reaction force to a pushing force that is exerted onto the cartridge body when manually displacing the liquid drug cartridge against the cartridge piston advancement direction. In subsequent step (b), the force for displacing the cartridge piston is generated as pulling force by the dosing unit and is transmitted to the cartridge piston via the liquid drug.

In step (a), liquid drug and/or gas (in particular air) that may be present in the liquid drug cartridge is forced out of the liquid drug cartridge and into a fluidic channel that couples the liquid drug cartridge with the filling port of the dosing unit, thereby priming the fluidic channel at least partly. In dependence of the amount of liquid drug that is forced out of the liquid drug cartridge in step (a), the fluidic channel may also be fully primed. Further, liquid drug may be forced into the dosing cylinder. In step (b), liquid drug is actively sucked into the dosing cylinder by increasing its volume. At the end of step (b), the fluidic channel should be fully primed, i. e. filled with liquid drug.

For both steps (a) (b), the valve unit is favourably in the filling state. Therefore, the dosing unit may be provided with the filling valve being in the filling state, or the method may include, prior to carrying out step (a), switching the valve unit into the filling state. Optionally, the method may further include determining a state if the valve unit and switching the valve unit into the filling state if it is in the draining state. Favourably, the dosing piston is in a most retracted position, such that the fluidic volume of the dosing cylinder is maximal in step (a). Such setup is favourable in order to provide maximum space for the air that is normally present in the fluidic system in an initial state and is compressed in step (a) when the cartridge piston is advanced. With the dosing piston in the most retracted position the resulting compression is minimal.

The direction into which the cartridge piston is displaced for reducing the liquid-filled volume of the liquid drug cartridge is referred to as cartridge piston advancement direction and corresponds to an advancement direction along the longitudinal axis of the (generally cylindrical) cartridge respectively cartridge body from its open rear end towards its open closed end where the drug cartridge outlet is located. Similarly, the direction into which the dosing piston is displaced for reducing the fluidic volume of the dosing cylinder is referred to as dosing piston advancement direction. The direction into which the dosing piston is displaced for increasing the fluidic volume of the dosing cylinder is referred to as dosing piston retraction direction.

The initialization pushing force in step (a) consequently acts on the rear end of the cartridge piston. In step (b), the cartridge displacement is caused by a fluidic sucking force that is exerted by the liquid drug inside the cartridge onto the liquid-contacting front end of the liquid drug cartridge.

In an initial state, before the cartridge piston is displaced by the initialization distance, it is typically in a most rear position where the rear end of the cartridge piston is flush with the rear circumferential edge of the cartridge body, or is slightly displaced towards the inner of the cartridge body.

According to an aspect, the overall objective is achieved by providing an ambulatory infusion system. The ambulatory infusion system includes a liquid drug cartridge, the liquid drug cartridge including a cartridge body and a cartridge piston. The cartridge piston is arranged inside the cartridge body in a sealing and displaceable manner.

The ambulatory infusion system further includes a dosing unit, the dosing unit including a metering pump unit with a dosing cylinder and a dosing piston. The dosing piston is arranged inside the dosing cylinder in a sealing and displaceable manner. The dosing unit further includes a valve unit with a filling port, and a draining port. The valve unit is configured for switching between a filling state and an alternative draining state. The filling port is fluidic coupled with an inner volume of the dosing cylinder in the filling state and the draining port is fluidic coupled with the inner volume of the dosing cylinder in the draining state.

The ambulatory infusion system further includes an initialization force member and an abutment member. The initialization force member being designed to exert a pushing force only. That is, the initialization force member cannot exert a pulling or retaining force.

The ambulatory infusion system further includes an electric pump drive in operative coupling with the dosing piston and an electronic control unit in operative coupling with the pump drive. The electronic control drive is configured to control operation of the pump drive.

The dosing unit, the initialization force member and the abutment member are arranged such that, by coupling the cartridge piston with the abutment member via the initialization force member, the initialization pushing force is exerted by the initialization force member acting between the cartridge piston and the abutment member. Thereby, the cartridge piston is displaced inside the cartridge body in a cartridge piston advancement direction by an initialization distance.

The control unit is configured to activate the pump drive to displace the dosing piston, thereby sucking liquid drug out of the liquid drug cartridge into the dosing cylinder and further displacing the cartridge piston inside the cartridge body in the cartridge piston advancement direction without the initialization pushing force being exerted.

In some embodiments, the ambulatory infusion system includes a device housing, the device housing enclosing the pump drive and the control unit. The device housing may be further designed to receive the liquid drug cartridge and to receive the dosing unit at least in part, wherein the abutment member is part of or rigidly coupled to the device housing. The components that are enclosed by the device housing form a common integral unit.

Typically, the ambulatory infusion system further includes an electric valve drive in operative coupling with the valve unit for switching the valve unit by activating the valve drive, between the filling state and the draining state. In some embodiments, a common drive serves as pump drive and valve drive. Alternatively, separate drives are provided and controlled separately. The coupling between the pump drive and the dosing piston, as well as the coupling between the valve drive and the valve unit, is releasable, thereby allowing a replacement of the dosing unit.

The dosing unit and the liquid drug cartridge are typically single-use products that are designed for a considerably shorter application time as compared to the ambulatory infusion device. The dosing unit may be provided separate from or readily connected with the liquid drug cartridge as common disposable unit. Such design, however, is not essential.

Generally, an embodiment of an ambulatory infusion system in accordance with the present disclosure may be designed to carry out an embodiment of a method in accordance with the present disclosure. Therefore, references to any components or structural features that are mentioned in the context of a method may be present in a corresponding embodiment of an ambulatory infusion system, even if not explicitly mentioned, and vice versa.

In an embodiment, the method includes, after carrying out step (a) and before carrying out step (b), carrying out a sequence of steps (a1), (a2), (a3). In step (a1) the valve unit is switched from the filling state into the draining state. In subsequent step (a2), the fluidic volume of the dosing cylinder is decreased by displacing the dosing piston, thereby forcing air and/or liquid out of the dosing cylinder via the draining port. Step (a2) is typically carried out by corresponding actuation of the electric pump drive. In subsequent step (a3), the valve unit is switched form the draining state into the filling state. Subsequent to step (a3), step (b) as explained before is carried out. In step (a2), the fluidic volume of the dosing cylinder is favourably reduced to a minimal volume that is typically negligible. The control unit of an ambulatory infusion device may be configured to control the execution of steps (a1, a2, a3).

In an embodiment, the method includes providing an abutment member, wherein the initialization pushing force is exerted by the initialization force member acting between the cartridge piston and an abutment member. The abutment member may be part of the ambulatory infusion system, and may in particular be part of or coupled to the device housing. The abutment member absorbs the initialization pushing force.

In an embodiment, the initialization force member includes a rigid pusher. The rigid pusher may, e. g. have the form of an elongated piston or plunger and be axially aligned with the liquid drug cartridge.

In an embodiment, the initialization force member includes a compression spring. The compression spring exerts the initialization pushing force in the compressed state and is relieved as the cartridge piston is advanced. Favourably, the compression spring is also relived in an initial configuration and is tensioned or loaded by displacing the liquid drug cartridge against the cartridge piston advancement direction.

In an embodiment, the initialization force member is permanently coupled to and/or formed integral with the abutment member. In a particular embodiment, the abutment member is provided as part of a device housing or permanently coupled to the device housing. Step (a) is carried out while inserting the liquid drug cartridge in the device housing against the cartridge piston advancement direction. In such embodiment, the initialization force member may in particular be part of an ambulatory infusion device and may project from the ground of a cartridge compartment into the cartridge compartment. As the piston is advanced by a fluidic sucking pressure in step (b) and subsequently during application, the initialization force member is separated from respectively loses contact with the cartridge piston and remains coupled with the abutment member.

In an embodiment, the initialization force member is permanently coupled to and/or formed integral with the cartridge piston. As the piston is advanced by a fluidic sucking pressure in step (b) and subsequently during application, the initialization force member stays coupled and is advanced with the cartridge piston and is separated from respectively loses contact with the abutment member.

In an embodiment, a cartridge body coupling member is provided. The cartridge body coupling member is designed for coupling with the cartridge body. The cartridge body coupling member is further designed for coupling with the device housing, thereby displacing the cartridge body against the cartridge piston advancement direction and coupling the cartridge piston with the abutment member via the initialization force member. In an assembled state where the cartridge body coupling member is coupled with both the cartridge body and the device hosing, the cartridge body is axially clamped between the cartridge body coupling member at the front side of the cartridge and a corresponding abutment element, e. g. the ground of a cartridge compartment, at the rear side of the cartridge body. The cartridge body coupling member may especially include a front cartridge body abutment member for abutting the cartridge front. The cartridge body coupling member serves as axial cartridge body fixing member. Alternatively or additionally, other types of axial cartridge body fixing members may be provided of axially fixing the cartridge body, e. g. axial and/or radial clamping members as part of the ambulatory infusion device.

In an embodiment, a cartridge body coupling member and the dosing unit are provided as common integral unit. Such common integral unit may especially be a disposable unit that is designed for coupling with an ambulatory infusion device as explained before.

In an embodiment, by coupling the cartridge body with the cartridge body coupling member, a fluidic connection is established between drug cartridge outlet and the filling port.

In an alternative embodiments, the liquid drug cartridge and the dosing unit may be provided as pre-assembled unit, typically a disposable unit. In such embodiment, a fluidic connection is present between the liquid drug cartridge outlet and the filling port from beginning on. The pre-assembled unit is designed for coupling with the device housing.

In an embodiment, the drug cartridge outlet is provided with a pierceable septum, the pierceable septum initially sealing the drug cartridge outlet. The cartridge body coupling member is provided with a piercing cannula, wherein establishing the fluidic connection between drug cartridge outlet and the filling port includes the piercing cannula piercing the pierceable septum.

In an embodiment, an electric pump drive is provided and operatively coupled with the dosing piston. Step (b) is carried out by activating the electric pump drive.

EXEMPLARY EMBODIMENTS

In the following, exemplary embodiments are explained with additional reference to the figures. Identical or analogue features are generally designated with identical reference numbers through the figures. Further, identical features may not be referenced in all figures for the sake of clarity.

Figure 1:
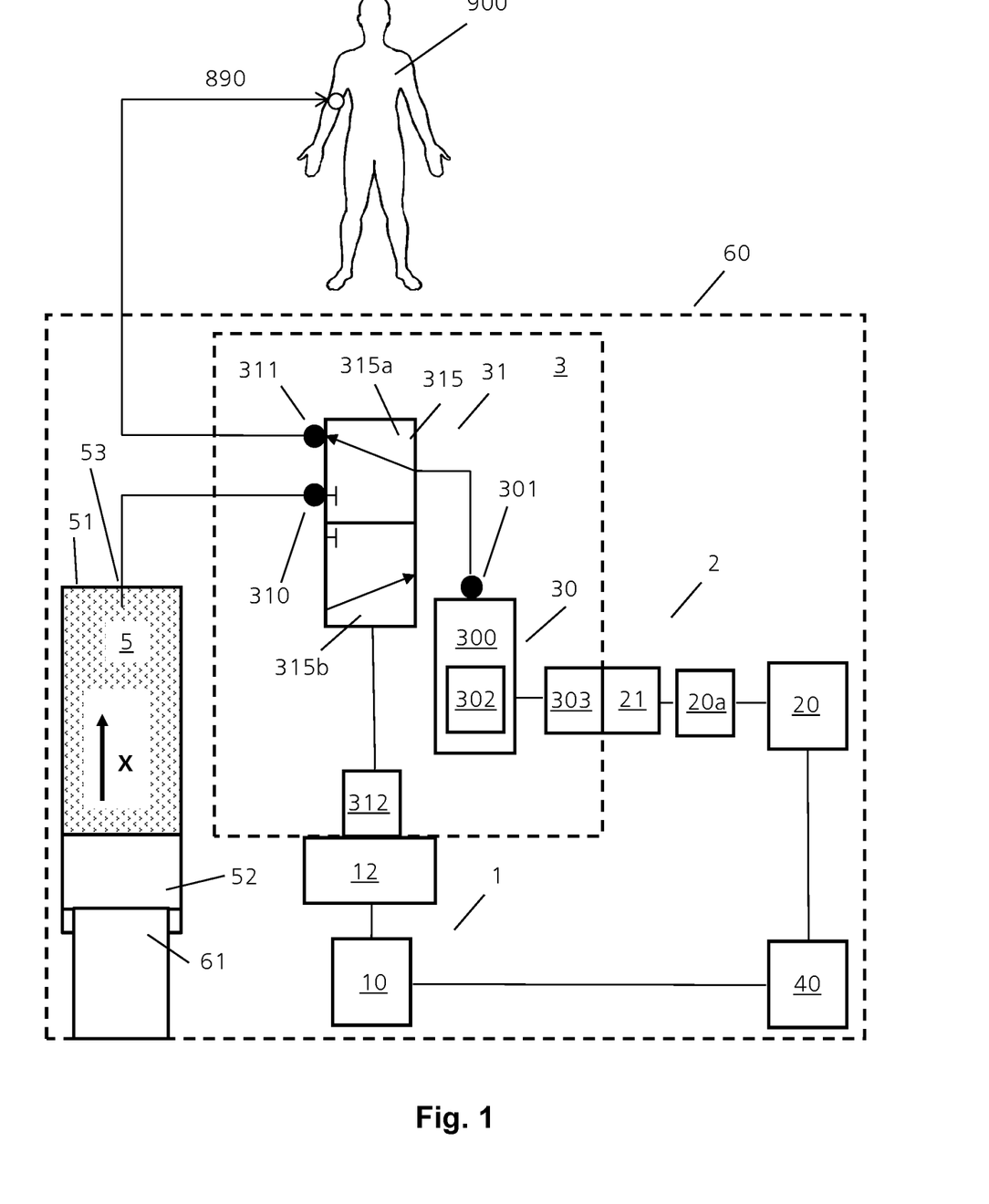
FIG. 1 schematically shows an ambulatory infusion system in accordance with the present disclosure.

In the following, reference is first made to FIG. 1. FIG. 1 shows functional units of an ambulatory infusion system in accordance with the present disclosure in a schematic operational configuration.

The ambulatory infusion system includes a dosing unit 3, a pump drive 2 and a valve drive 1. The ambulatory infusion system further includes an electronic control unit 40. The ambulatory infusion system further includes, a liquid drug reservoir in form of a liquid drug cartridge 5. It is to be noted that only those structural and functional units are shown that are of particular relevance in view of the present disclosure. Other units, such as power supply, user interface etc. are typically present as well.

The dosing unit 3 includes a metering pump unit 30 (also referred to as pump unit) and a valve unit 31. The metering unit 30 includes a dosing cylinder 300 and a dosing piston 302 that is arranged inside of the dosing cylinder 300 in a sealing and displaceable manner, similar to a syringe. In a proximal front wall of the dosing cylinder 300, a bore is arranged as pump port 301 that fluidic couples the inner volume of the dosing cylinder 300 with the valve unit 31. By displacing the dosing piston 302 along a dosing cylinder axis towards the pump port 301, the liquid-filled filled fluidic volume of the dosing cylinder 300 may be decreased, thereby expelling liquid drug out of the dosing cylinder 300. Similarly, by displacing the dosing piston 302 along the dosing cylinder axis in an opposite direction, away from the pump port 301, the liquid-filled fluidic volume of the dosing cylinder 300 may be increased, thereby sucking liquid drug into the dosing cylinder 300.

The valve unit 31 includes a shutoff body 315 that is movable between a filling position 315b and a draining position 315a. If the shutoff body is in the filling position, the valve unit is referred to as being in a filling state.

Likewise, if the shutoff body 315 is in the draining position, the valve unit 31 is referred to as being in the draining state. During operation, the valve unit 31 is repeatedly switched between the filling state and the draining state as explained further below in more detail. The reservoir 5 is fluidic coupled to the valve unit 31 via a filling port 310. A patient 900 is fluidic coupled to the valve unit 31 via a draining port 311 and an infusion site interface 890. It is noted that the infusion site interface 890 is exemplarily shown as integral with an infusion line, e.g. a catheter. Alternatively, the infusion pump device may be designed as a patch pump that is directly attached to a patient's body, e. g., via an adhesive pad. Here, the infusion site interface may be directly a cannula.

The valve unit 31 includes a shutoff body 315 that is sealing and rotatable arranged in a valve bearing. The shutoff body 315 includes a fluidic channel arrangement that realizes, in dependence of a rotational position of the shutout body 315, either the filling state 315b or the draining state 315a, respectively. The valve unit 31 is typically arranged in line with and proximal from the pump unit 30. In a typical arrangement that is also assumed in the following, the shutoff body axis is parallel to and optionally coincides with the dosing cylinder axis (axis along which the dosing piston 302 is displaced). This arrangement, however, is not essential.

The dosing unit 3 further includes, as part of the valve unit 31, a valve driver coupler 312 for switching the valve unit 31 between the filling position, 315b, and the draining position 315a. Similarly, the dosing unit 3 includes, as part of the metering pump unit 30, a pump driver coupler 303 for displacing the dosing piston 302 inside the dosing cylinder 300 as explained before. The pump driver coupler 303 may be fully or partly integral with the dosing piston 302.

The operation of the metering unit 30 and the valve unit 31 is exemplarily independent from each other. That is, the dosing piston 302 may be displaced inside the dosing cylinder 300 without affecting the state of the valve unit 31. Likewise, the state of the valve unit 31 may be changed respectively switched without affecting the position of the dosing piston 302 inside the dosing cylinder 300. Further, a valve switching between the filling state and the draining state does not involve a liquid displacement between the filling port 310 and the draining port 311, resulting from the movement of the shutoff body 315. Consequently, a valve switching does not involve the dosing of liquid to the patient. This aspect is of particular relevance because the controlled and metered dosing is carried out exclusively by controlled displacement of the dosing piston 302. For highly concentrated drugs such as typical liquid insulin formulations, an unintended drug administration that may result from the valve switching may cause undesired and potentially severe medical complications.

In a typical arrangement, the dosing unit 3 with the metering pump unit 30 and the valve unit 31 is formed as a compact device and in an integral way. Therefore, the pump port 301 is, in contrast to the filling port 310 and the draining port 311, not accessible from outside the dosing unit 3. In a typical embodiment, the dosing cylinder has an inner diameter in a range of 3 mm to 5 mm, and the travel distance of the dosing piston 302 is in a range of 5 mm to 15 mm.

Figure 2A:
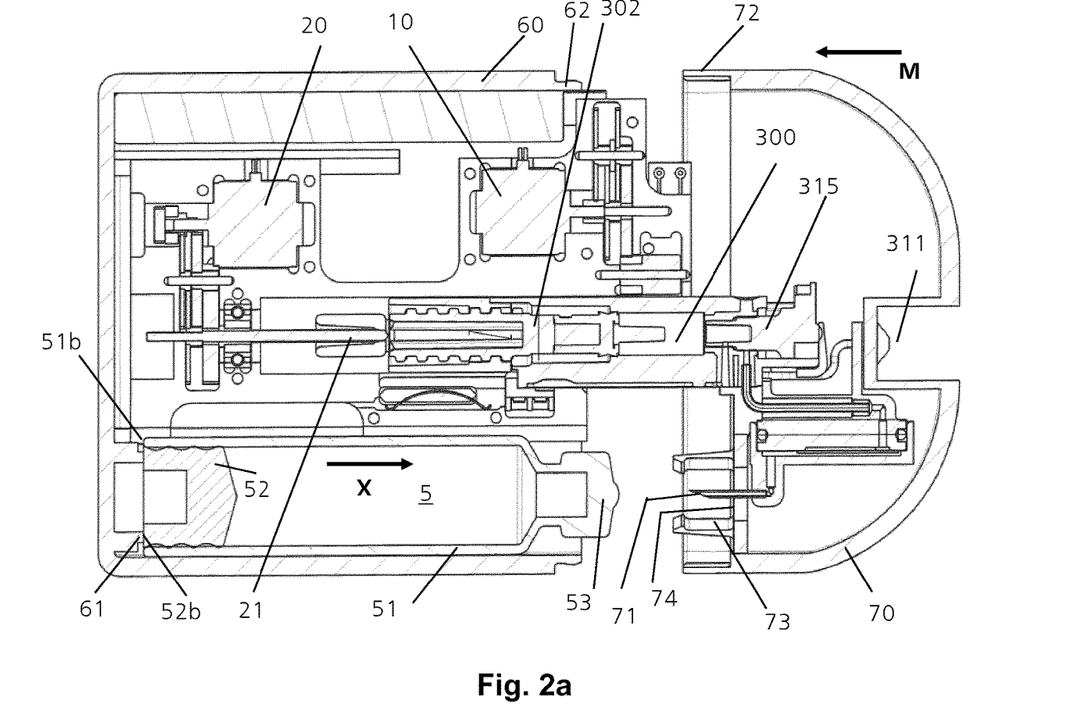
FIGS. 2a, 2b 2c show an ambulatory infusion system in various states during initialization.
Figure 2B:
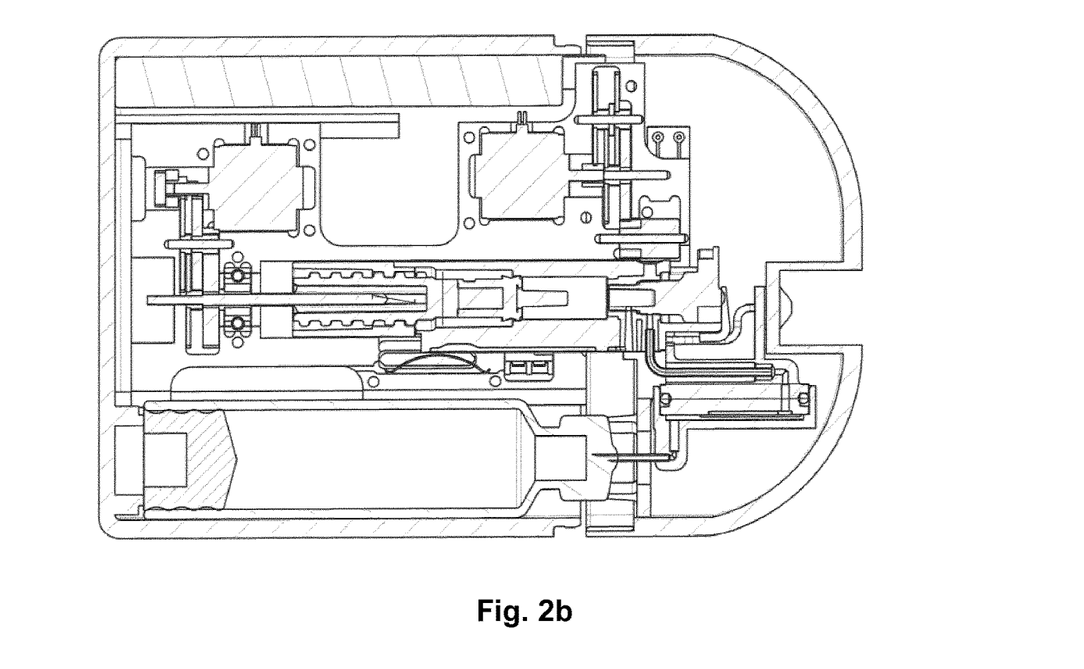
Figure 2C:
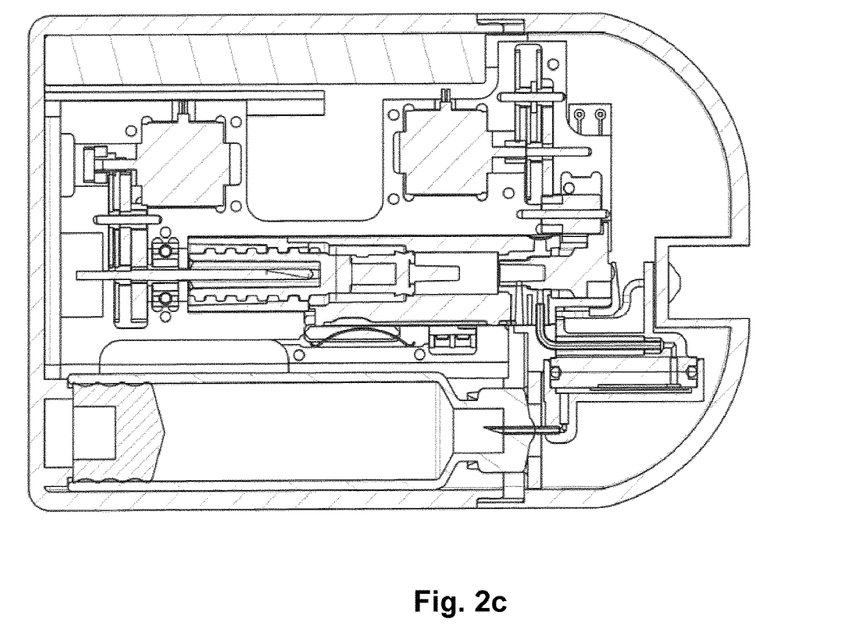

With respect to the valve unit 31, it is further noted that FIG. 2 only shows the states 315a, 315b where either of the filling port 310 or the draining port 311 is coupled to the pump port 301. In a further intermediate state, however, all three ports 301, 310, 311 are closed, resulting in fluidic isolation. In a typical embodiment and mode of operation, however, such intermediate state is only assumed during switching operations for a negligible transient period.

The pump drive 2 includes the pump driver 21 that is designed to releasable engage the pump driver coupler 303 for displacing the dosing piston inside the dosing cylinder 300 as explained before in both the advancement direction and the retraction direction. The pump drive 2 further includes a pump actuator 20 that typically includes a motor, a, standard DC motor, a stepper motor or electronically commutated respectively brushless DC motor. The pump drive 2 further includes a gear 20a with a reduction gear and a rotatory-to-linear transformation gear, in particular a spindle drive or screw drive, that transforms a rotatory actuator movement into a reversible linear displacement movement of the pump driver 21, and, via the pump driver coupler 303, of the dosing piston 302. The pump driver 21 may be realized as plunger. The pump driver coupler 303 may be firmly attached to or integrated into a distal portion of the dosing piston 302. The pump driver 21 and the pump driver coupler 303 are designed for push-pull-coupling, e.g. as bayonet coupling, snap-fit coupling, or the like. A reciprocal movement of the pump driver 21 results in a corresponding reciprocal dosing piston movement in proximal or distal direction, respectively.

Alternatively, the pump driver 21 is realized as drive nut or threaded spindle, and the pump driver coupler is respectively as threaded spindle respectively as nut.

The valve drive 1 includes a valve actuator 10 and a valve driver 12 that is designed for coupling with the valve driver coupler 312. Exemplary embodiments of the valve drive 11 and the valve driver coupler 312 are disclosed in the European Patent Application 16173361.3 and WO2015/082305 to the disclosure of which reference is reference is herewith made.

The control unit 40 controls the overall operation of the ambulatory infusion device and ambulatory infusion system and in particular the valve actuator 10 and the pump actuator 20. The control unit 40 typically includes one or more microcomputers and/or microcontrollers with corresponding computer program code respectively firmware for controlling operation of the ambulatory infusion system. The control unit 40 typically further includes peripheral circuitry as known in the art.

The liquid drug cartridge 5 has a cylindrical cartridge body 51 with a generally closed front end and an open rear end. A cartridge piston 52 is arranged inside the cartridge body 51 in a sealing manner and is displaceable along a longitudinal cartridge axis. A drug cartridge outlet is arranged at the front the cartridge body 51 in a cap 53 and sealed a by a pierceable septum. The fluidic connection with the filling port 310 is established via a hollow piercing cannula (not separately referenced. The portion of the inner volume of the cartridge body 5 between its front wall and the cartridge piston 52 is filled with liquid drug. In an initial state, the cartridge piston 52 is typically in a substantial rear-most position and the liquid drug volume is maximal. By displacing the cartridge piston 52 along the longitudinal cartridge axis in the cartridge piston advancement direction X, the liquid volume is reduced.

Typically, the cartridge body 51 is made from medical-grade glass or plastics and may have friction-reducing coating (e. g. on silicone-basis) on tis inside. The cartridge piston 52 is typically made from medical-grade rubber or may have a piston body from hard plastics and one or more circumferential soft sealing(s). The cartridge 5 may, as a whole, e. g. be a so called pen cartridge as used in pen-type injection devices, in particular insulin injection devices.

The device housing 60 further serves as abutment member for an initialization force member 61 that is, in an operational configuration, arranged between the device housing 60 and the cartridge piston 52.

The pump drive 2, the valve drive 1 and the control circuitry 40 typically belong to an ambulatory infusion device as common compact device with the device housing 60 that permanently e these units, as well as optionally further units such as a user interface and a power supply. The ambulatory infusion device is designed for an extended lifetime of a number of months, e. g. six months, or even a number of years, while the dosing unit 3 and the reservoir 5 are disposable and of substantially shorter lifetime of typically a number of days up to, e. g. two weeks, in dependence of the patient's individual drug needs. The valve driver 12 and the pump driver 21 of the ambulatory infusion device, as well as the pump driver coupler 303 and the valve driver coupler 312 of the dosing unit 3 are therefore designed for releasable coupling in the sense that coupling as explained before between the pump driver 21 and the pump driver coupler 303, respectively between the valve driver 12 and the valve driver coupler 312 can be released without damaging the pump driver 21 and the valve driver 12.

In the following, reference is additionally made to FIG. 2a to FIG. 2c, showing an ambulatory infusion system in accordance with the present disclosure, e. g. an ambulatory infusion system according to FIG. 1, in various states during initialization.

In the example of FIG. 2a to FIG. 2c, the dosing unit 3 is realized in an integral way with a disposable housing 70, thereby forming a disposable unit. The disposable housing 70 comprises mating coupling members 72 that are designed for releasable coupling, e. g. snap-fit coupling with corresponding mating connectors 62 of the device housing 60, thereby establishing a favourably non-permanent and water-tight connection. The coupling is achieved by displacing the disposable housing 70 with the dosing unit 3 in a mating direction M relative to the device housing 60.

The disposable housing 70 comprises a cartridge body coupling member that includes resilient fingers 73 that are designed to snap behind a restricted neck portion not referenced) of the cartridge body 50, thereby coupling the resilient fingers 73 and the disposable housing 70 with the cartridge body 50, The cartridge body coupling member further includes a front cartridge abutment member 74 that is designed to abut the front end of the cartridge body 51. The front cartridge abutment member 74 is surrounded by the resilient fingers 73 and is exemplarily formed integral with the disposable housing 70, Further, a piercing cannula 71 is provided that projects from the centre of the front cartridge abutment member 74, substantially parallel to the resilient fingers 73, Via a fluidic channel that is arranged in respectively integrated into the disposable housing 70 and/or the dosing unit 3, the piercing cannula 71 is fluically coupled with the inlet port 310. It is assumed that the valve unit 31 is in the filling state for the following steps, If required, the valve drive 10 may be activated in a preparatory step to switch the valve unit 31 into the filling state.

FIG. 2a shows an intermediate situation during the process of coupling the device housing 60 with the disposable housing 70. In FIG. 2a, the disposable housing 70 and the device housing 60 are somewhat spaced apart from each other, while the closing unit 3 is partly seated in a corresponding compartment (not referenced) of the device housing 60. The liquid drug cartridge 5 has been inserted into a corresponding cartridge compartment (not referenced) of the device housing 60 where it rests, in the configuration of FIG. 2a, in a loose and substantially force-less state.

FIG. 2b shows the situation somewhat later in a configuration during the coupling of the infusion device housing 60 and the disposable housing 70. In FIG. 2a, the piercing cannula 71 has partly, penetrated the pierceable septum, and the resilient fingers 73 pass along the circumference of the cap 53. It is noted that the rear end 52b of the cartridge piston 52 abuts against the front end (not referenced) of the initialization force member 61, while the rear end 51b (circumferential rear edge) of the cartridge body 51 is not supported and free to move. The force that results from the contact between the piercing cannula 71 and the septum as well as between the resilient fingers 73 and the cap 53 is accordingly transmitted from the cartridge body 51 via the frictional engagement between the cartridge body 51 and the piston 52 to the initialization force member 61 is finally absorbed by the abutment member that is realized by the device housing 60. The initialization force member 61 accordingly exerts an initialization pushing force onto the cartridge piston 51 via its rear end 51b in the piston advancement direction X.

As long as the force that is transmitted from the cartridge body 51 to the cartridge piston 52 is below the sticking force, both the cartridge body 51 and the cartridge piston 52 stay in place and do not move axially. The sticking force may be in a range of about 10 Newton or even more.

At some point, the front cartridge abutment member 74 hits the front end of the cap 53. Further advancement of the disposable housing 70 in the mating direction will accordingly result in the cartridge body 51 being axially pushed along the longitudinal cartridge axis in the mating direction M respectively the against the cartridge piston displacement direction X.

Since the cartridge piston 52 abuts the initialization force member 61 and is therefore, in contrast to the cartridge body 51, not free to move against the cartridge piston displacement direction X, the force between the cartridge body 51 and the cartridge piston 52 will steeply increase and finally overcome the sticking friction. Pushing the cartridge against the cartridge piston displacement direction X now accordingly results in a relative displacement of the cartridge piston 52 inside the cartridge body in the cartridge piston advancement direction.

FIG. 2c shows the final mating configuration where the mating coupling members 72 and 62 are in engagement with each other, the resilient fingers have snapped around the cap 53 and clamp the cartridge body 53 due to the constructed neck portion, and the piercing cannula 71 has fully penetrated the septum, accordingly establishing a fluidic contact between the inner volume of the cartridge body and the inlet port 310. Now, the rear end 51b of the cartridge body 51 abuts the ground of the cartridge compartment around the initialization force member 61. The cartridge body 51 with the cap 53 is accordingly axially clamed between the device housing 60 and the front cartridge abutment member 74.

The initialization distance by which the cartridge piston 52 is displaced relative to the cartridge body 51 depends of the relative positions of the front end of the initialization force member 61, the rear end 52b of the cartridge piston 52, and the rear end 51b of the cartridge body 51. A typical initialisation distance is in a range of some tens of a millimetre but may also be in a range of up to e. g. 2 mm in dependence of the overall design.

When displacing the cartridge piston 52 by the initialization distance, a corresponding amount of liquid drug is generally displaced out of the drug cartridge 5 and towards the dosing unit 3. However, since some amount of air may initially be present in the liquid drug cartridge 5, it may also be a mixture of air and liquid.

After establishing the configuration of FIG. 2c, the valve is switched to the drain state. Then the pump drive 2 is activated to displace the dosing piston 302 into the dosing piston advancement direction, thereby minimizing the fluidic volume of the dosing cylinder 300 and emptying it from that mixture of air and liquid. Thereafter, the valve unit is switched back to the filling state. Subsequently, the dosing cylinder is filled, e. g. fully, filled, with liquid drug by displacing the dosing piston into the dosing piston retraction direction. Typically, this movement of the dosing piston ends in a most retracted or retracted end position where the fluidic volume of the dosing cylinder is maximal.

The mechanical coupling between the initialization force member 61 and the cartridge piston 52 is a one-way pushing connection. That is, the initialization force member 61 can exert a pushing force onto the cartridge piston 52 in the piston advancement direction, but cannot retain the cartridge piston 52. When increasing the fluidic volume of the dosing cylinder 300, an under pressure is accordingly generated inside the dosing cylinder 300 and liquid drug is sucked out of the liquid drug cartridge 5 and into the dosing cylinder. Because the liquid drug is substantially incompressible, a corresponding suction force is exerted onto the cartridge piston 52 and the cartridge piston is displaced in the cartridge piston advancement direction X. As soon as the cartridge piston 52 starts displacing, its rear end 52b losses contact with the initialization force member. This situation remains for the further operation of the ambulatory infusion system until the liquid drug cartridge is finally emptied.

The amount of liquid drug that is sucked into the dosing cylinder 300 in the before-described step favourably corresponds at least to the fluidic volume of the fluid path from the liquid drug cartridge to the inlet port 315, such that the fluid path between liquid drug cartridge 300 and dosing unit 3 is fully filled with liquid. The fluid volume may, however, also be somewhat larger.

The sucking force for displacing the cartridge piston 52 in the cartridge piston advancement direction X must be generated by the dosing unit 3. While the initial frictional sticking force of fresh liquid drug cartridge may be greater than the sucking force that can be generated, this initial frictional sticking force is, in accordance with the present disclosure, overcome by the initialization force member. Once this is case, both the frictional sticking force and the frictional gliding force are significantly lower and can be overcome by a small under pressure.

Figure 3:
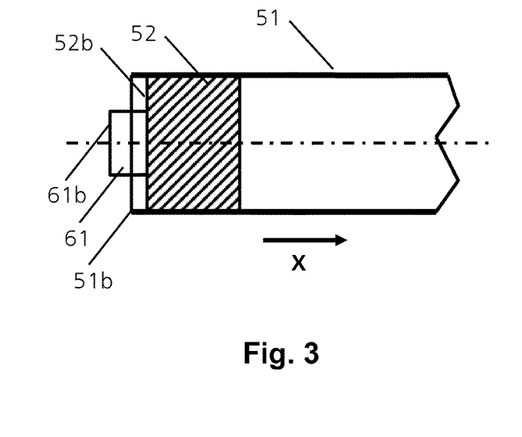
FIG. 3 shows an embodiment of a liquid drug cartridge with an initialization force member.

In the following, reference is additionally made to FIG. 3. FIG. 3 schematically shows the rear section of a cartridge 15 that may be generally designed similar to the cartridge body shown in FIG. 2a to FIG. c. In the embodiment of FIG. 3, however, the initialization force member 61 has the shape of a disc or plunger and is formed integrally with or is rigidly attached to the cartridge piston 52 and is accordingly part of the liquid drug cartridge 5. The initialization force member 61 projects from the rear end 52b of the cartridge piston 52 in rear direction (against the cartridge piston advancement direction X). In an initial position of the cartridge piston 52, the rear end 61b of the initialization force member 61 is rear from the rear end 51b of the cartridge body 51.

Upon insertion of the cartridge 5 into the device housing 60, the initialization force member 61 will interact with housing 60 respectively the ground of the cartridge compartment as abutment member in substantially the same way as explained before in the context of FIG. 2a to FIG. c. The connection between the rear end 61*b* of the initialization force member 61 and the abutment member is a one-way pushing connection as explained before. Subsequent to exerting the initialization force and displacing the cartridge piston 52 by the initialization distance, further advancement of the cartridge piston 52 that results from sucking liquid drug out of the cartridge 5 accordingly results in the connection between the rear end 61*b* and the abutment member being lost. Consequently, the initialization force member moves along with the cartridge piston 52. The lateral dimensions (traverse to the longitudinal cartridge axis) of the initialization force member 61 are smaller than the inner diameter of the cartridge body 51 and the piston 52, thus along the initialization force member 61 to be received by and move within the inner volume of the cartridge body 51.

Figure 4:
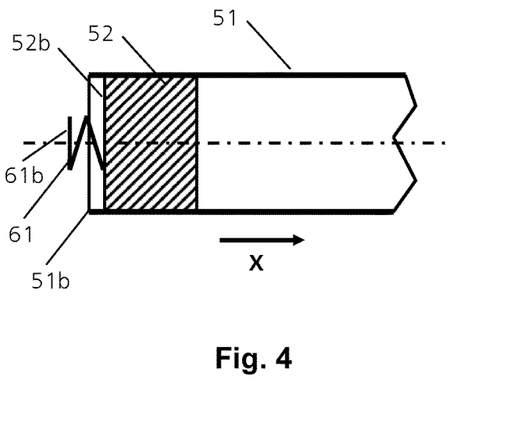
FIG. 4 shows further embodiment of a liquid drug cartridge with an initialization force member.

In the following, reference is additionally made to FIG. 4. The embodiment of FIG. 4 is similar to the embodiment of FIG. 3. In the embodiment of FIG. 4, however, the initialization force member 61 is realized as a short compression spring of high stiffness, with a spring constant in a range of e. g. 15 to 25 N/mm. while the tensioning distance depends form the volume to be filled during step a) of the sequence. The maximal tensioning force exceeds in any case the sticking force of the reservoir piston. The spring is unloaded during storage prior to insertion into the device housing 60 respectively the cartridge compartment and is compressed only when attaching the disposable housing 70 as explained before. In a variant, the spring is not attached to the cartridge piston 51 but to the device housing 60 and projects from the ground of the cartridge compartment.

The invention claimed is:

1. A method for initializing an ambulatory infusion system comprising:
    providing a liquid drug cartridge, the liquid drug cartridge including a cartridge body and a cartridge piston, the cartridge piston being arranged inside the cartridge body in a sealing and displaceable manner;
    providing a dosing unit, the dosing unit including a metering pump unit with a dosing cylinder having an inner volume and a dosing piston received inside the dosing cylinder in a sealing and displaceable manner, the dosing unit further including a valve unit with a filling port and a draining port, the valve unit being configured for switching between a filling state and an alternative draining state, wherein the filling port is fluidically coupled with the inner volume of the dosing cylinder in the filling state and the draining port is fluidically coupled with the inner volume of the dosing cylinder in the draining state; and
    providing a device housing configured to receive the liquid drug cartridge and the dosing unit, the device housing including an initialization force member configured to displace the cartridge an initialization distance upon insertion of the cartridge into the device housing;
    a) inserting the liquid drug cartridge into the device housing and thereby exerting with the initialization force member, an initialization pushing force onto the cartridge piston and displacing the cartridge piston inside the cartridge body in a cartridge piston advancement direction (X) by an initialization distance; and
    b) increasing a fluidic volume of the dosing cylinder by displacing the dosing piston, thereby sucking liquid drug out of the liquid drug cartridge into the dosing cylinder and further displacing the cartridge piston inside the cartridge body in the cartridge piston advancement direction (X), without the initialization pushing force being exerted.

2. The method according to claim 1, the method including providing an abutment member, wherein the initialization pushing force is exerted by the initialization force member acting between the cartridge piston and the abutment member.

3. The method according to claim 2, wherein the initialization force member includes a rigid pusher.

4. The method according to claim 2, wherein the initialization force member includes a compression spring.

5. The method according to claim 1, the method including providing an electric pump drive, operatively coupling the electric pump drive with the dosing piston, and carrying out step (b) by activating the electric pump drive.

6. A method for initializing an ambulatory infusion system, comprising:
    providing a liquid drug cartridge, the liquid drug cartridge including a cartridge body and a cartridge piston, the cartridge piston being arranged inside the cartridge body in a sealing and displaceable manner;
    providing a dosing unit, the dosing unit including a metering pump unit with a dosing cylinder having an inner volume and a dosing piston received inside the dosing cylinder in a sealing and displaceable manner, the dosing unit further including a valve unit with a filling port and a draining port, the valve unit being configured for switching between a filling state and an alternative draining state, wherein the filling port is fluidically coupled with the inner volume of the dosing cylinder in the filling state and the draining port is fluidically coupled with the inner volume of the dosing cylinder in the draining state; and
    providing a device housing configured to receive the liquid drug cartridge and the dosing unit, the device housing including an initialization force member configured to displace the cartridge an initialization distance upon insertion of the cartridge into the device housing;
    providing an abutment member, wherein the initialization force member is permanently coupled to and/or formed integral with the abutment member;
    a) inserting the liquid drug cartridge into the device housing and thereby exerting with the initialization force member, an initialization pushing force onto the cartridge piston and displacing the cartridge piston inside the cartridge body in a cartridge piston advancement direction (X) by an initialization distance, wherein the initialization pushing force is exerted by the initialization force member acting between the cartridge piston and the abutment member; and
    b) increasing a fluidic volume of the dosing cylinder by displacing the dosing piston, thereby sucking liquid drug out of the liquid drug cartridge into the dosing cylinder and further displacing the cartridge piston inside the cartridge body in the cartridge piston advancement direction (X), without the initialization pushing force being exerted.

7. The method according to claim 5, wherein the abutment member is permanently coupled to and/or formed integral with the device housing.

8. A method for initializing an ambulatory infusion system, comprising:
    providing a liquid drug cartridge, the liquid drug cartridge including a cartridge body and a cartridge piston, the cartridge piston being arranged inside the cartridge body in a sealing and displaceable manner;

providing a dosing unit, the dosing unit including a metering pump unit with a dosing cylinder having an inner volume and a dosing piston received inside the dosing cylinder in a sealing and displaceable manner, the dosing unit further including a valve unit with a filling port and a draining port, the valve unit being configured for switching between a filling state and an alternative draining state, wherein the filling port is fluidically coupled with the inner volume of the dosing cylinder in the filling state and the draining port is fluidically coupled with the inner volume of the dosing cylinder in the draining state; and providing a device housing configured to receive the liquid drug cartridge and the dosing unit, the device housing including an initialization force member configured to displace the cartridge an initialization distance upon insertion of the cartridge into the device housing;

providing an abutment member, wherein the abutment member is provided as part of or permanently coupled to the device housing;

a) inserting the liquid drug cartridge into the device housing and thereby exerting with the initialization force member, an initialization pushing force onto the cartridge piston and displacing the cartridge piston inside the cartridge body in a cartridge piston advancement direction (X) by an initialization distance, wherein the initialization pushing force is exerted by the initialization force member acting between the cartridge piston and the abutment member wherein step (a) is carried out while inserting the liquid drug cartridge into the device housing opposite the cartridge piston advancement direction; and b) increasing a fluidic volume of the dosing cylinder by displacing the dosing piston, thereby sucking liquid drug out of the liquid drug cartridge into the dosing cylinder and further displacing the cartridge piston inside the cartridge body in the cartridge piston advancement direction (X), without the initialization pushing force being exerted.

9. The method according to claim 8, the method further including providing a cartridge body coupling member, coupling the cartridge body coupling member with the cartridge body, and coupling the cartridge body coupling member with the device housing, thereby displacing the cartridge body opposite the cartridge piston advancement direction (X) and coupling the cartridge piston with the abutment member via the initialization force member.

10. The method according to claim 9, the method including providing the cartridge body coupling member and the dosing unit as common integral units.

11. The method according to claim 8, wherein, the liquid drug cartridge includes a drug cartridge outlet, and wherein by coupling the cartridge body with the cartridge body coupling member, a fluidic connection is established between the drug cartridge outlet and the filling port.

12. The method according to claim 11, wherein the drug cartridge outlet is provided with a pierceable septum, the pierceable septum initially sealing the drug cartridge outlet, and the cartridge body coupling member is provided with a piercing cannula, wherein establishing the fluidic connection between the drug cartridge outlet and the filling port includes the piercing cannula piercing the pierceable septum.

13. An ambulatory infusion system, including:
a liquid drug cartridge, the liquid drug cartridge including a cartridge body and a cartridge piston, the cartridge piston being arranged inside the cartridge body in a sealing and displaceable manner;

a dosing unit, the dosing unit including a metering pump unit with a dosing cylinder and a dosing piston, the dosing piston being arranged inside the dosing cylinder in a sealing and displaceable manner, the dosing unit further including a valve unit with a filling port, and a draining port, the valve unit being configured for switching between a filling state and an alternative draining state, wherein the filling port is fluidically coupled with an inner volume of the dosing cylinder in the filling state and the draining port is fluidically coupled with the inner volume of the dosing cylinder in the draining state;

an initialization force member, the initialization force member being configured to exert an initialization pushing force only;

an abutment member, an electric pump drive in operative coupling with the dosing piston; and a control unit in operative coupling with the pump drive;

wherein the dosing unit, the initialization force member and the abutment member are arranged such that, by coupling the cartridge piston with the abutment member via the initialization force member, the initialization pushing force is exerted by the initialization force member acting between the cartridge piston and the abutment member, thereby displacing the cartridge piston inside the cartridge body in a cartridge piston advancement direction (X) by an initialization distance;

wherein the control unit is configured to activate the pump drive to displace the dosing piston, thereby sucking liquid drug out of the liquid drug cartridge into the dosing cylinder and further displacing the cartridge piston inside the cartridge body in the cartridge piston advancement direction (X) without the initialization pushing force being exerted.

14. The ambulatory infusion system according to claim 13, the ambulatory infusion system further including an electric valve drive in operative coupling with the valve unit for switching the valve unit, by activating the valve drive between the filling state and the draining state.

15. The ambulatory infusion system according to claim 13, further including a device housing, the device housing enclosing the pump drive and the control unit, the device housing being further configured to receive the liquid drug cartridge and to receive the dosing unit at least in part, wherein the abutment member is part of or rigidly coupled to the device housing.

16. An ambulatory infusion system comprising:
a device housing;
a dosing unit received within the device housing and including a dosing cylinder having an inner volume and a dosing piston received inside the dosing cylinder, the dosing unit further including a valve unit configured for switching the dosing unit between a filling state and a draining state; and
a liquid drug cartridge including a cartridge body and a cartridge piston received inside the cartridge body in a sealing and displaceable manner, the liquid drug cartridge being configured to be inserted into the device housing;
the device housing including an initialization force member configured upon initial insertion of the liquid drug cartridge to be received against the cartridge and then upon further insertion of the liquid drug cartridge to displace the cartridge piston inside the cartridge body in a cartridge piston advancement direction (X) by an initialization distance.

17. A method for initializing an ambulatory infusion system comprising:
providing an ambulatory infusion system according to claim 16; inserting the liquid drug cartridge to a first position having the cartridge piston received against the initialization force member and then further inserting the liquid drug cartridge to cause the initialization force member to press against and displace the cartridge piston inside the cartridge body in a cartridge piston advancement direction (X) by an initialization distance.

* * * * *